United States Patent [19]

Rosenberger et al.

[11] Patent Number: 4,954,275
[45] Date of Patent: Sep. 4, 1990

[54] USE OF PHENOL-MERCAPTOCARBOXYLIC ACID ESTERS AS STABILIZERS FOR LUBRICANTS

[75] Inventors: Siegfried Rosenberger, Riehen; Kurt Schwarzenbach, Pfeffingen, both of Switzerland

[73] Assignee: Ciba-Geigy Corporation, Ardsley, N.Y.

[21] Appl. No.: 932,431

[22] Filed: Nov. 19, 1986

Related U.S. Application Data

[60] Division of Ser. No. 919,605, Oct. 14, 1986, abandoned, which is a continuation-in-part of Ser. No. 347,399, Feb. 10, 1982.

Foreign Application Priority Data

Feb. 29, 1981 [CH] Switzerland ............ 1107/81

[51] Int. Cl.$^5$ .............................. C10M 135/26
[52] U.S. Cl. ................................. 252/48.6
[58] Field of Search ........................ 252/48.6

[56] References Cited

U.S. PATENT DOCUMENTS

| | | | |
|---|---|---|---|
| 3,346,648 | 10/1967 | Worrel | 260/611 |
| 3,745,147 | 7/1973 | Kleiner | 252/48.6 |
| 3,766,069 | 10/1973 | Holten | 252/48.6 |
| 3,789,064 | 1/1974 | Hechenbleikner et al. | 260/473 S |
| 3,810,869 | 5/1974 | Zaweski | 260/45.85 B |
| 3,832,328 | 8/1974 | Eggensperger | 252/48.6 |
| 3,919,097 | 11/1975 | Palk | 252/48.6 |
| 4,154,723 | 5/1979 | Hirsch et al. | 252/48.6 |
| 4,198,305 | 4/1980 | Okorodudu | 252/48.6 |
| 4,559,153 | 12/1985 | Baldwin et al. | 252/48.6 |
| 4,612,131 | 9/1986 | Rosenberger | 252/48.6 |

FOREIGN PATENT DOCUMENTS 1194466  10/1985  Canada ............... 252/48.6

OTHER PUBLICATIONS

Scott, "Atmospheric Oxidation and Antioxidants", 1965, pp. 124, 125.

*Primary Examiner*—Mark L. Bell
*Assistant Examiner*—Ellen McAvoy
*Attorney, Agent, or Firm*—Harry Falber

[57] ABSTRACT

The phenol-mercaptocarboxylic acid esters used for stabilizing elastomers are those of the formula

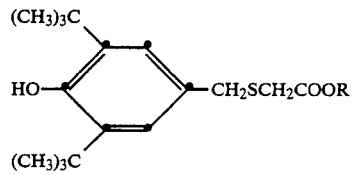

wherein R is $C_1$–$C_{18}$ alkyl.

3 Claims, No Drawings

USE OF PHENOL-MERCAPTOCARBOXYLIC ACID ESTERS AS STABILIZERS FOR LUBRICANTS

This is a divisional of application Ser. No. 919,605 filed on Oct. 14, 1986, now abandoned, which is a continuation-in-part application of application Ser. No. 347,399, filed Feb. 10, 1982.

The invention relates to the use of particular phenol-mercaptocarboxylic acid esters for stabilising organic polymers and lubricants.

German Patent Specification No. 1,288,604, which has already very broadly claimed phenol-mercaptocarboxylic acid esters and their use as stabilisers may be quoted as prior art. These phenol-mercaptocarboxylic acid esters are those of the formula a or b:

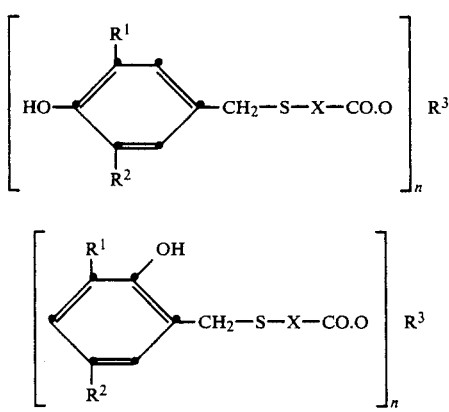

in which n is an integer from 1 to 4, $R^1$ and $R^2$ are identical or different, straight-chain or branched alkyl groups having 1 to 4 C atoms, $R^3$ is a linear, branched or cyclic alkyl group, a benzyl group, a thioether group or an ether group (if n=1), or an alkylene group (if n=2 to 4) having a total of 1 to 20 C atoms, and X is a straight-chain or branched alkylene group having 1 or 2 C atoms.

In the said patent specification, specific compounds of the formula a, in which $R^1$ and $R^2$ are the methyl group, are emphasised as being particularly advantageous in their action as stabilisers.

It has now been found that very specific esters of this group of products protected generically by the above German patent specification stand out particularly advantageously in their action as stabilisers and, in particular, are distinctly superior to the products of the formula a, mentioned in German Patent Specification 1,288,604, in which $R^1$ and $R^2$ are methyl.

The invention relates to the use of phenol-mercaptocarboxylic acid esters of the formula I

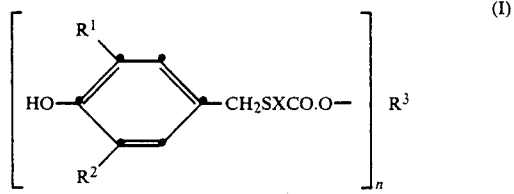

in which n is an integer from 1 to 4, $R^1$ and $R^2$ are identical or different and are $C_1$–$C_5$-alkyl or $C_5$–$C_8$-cycloalkyl, and X is methylene or ethylene, and in which $R^3$, in the case where n=1, is a hydrocarbon radical which may contain branched molecular groups and may contain —O— or —S— bridges, such as alkyl having in each case a total of 1 to 18 C atoms, $C_5$–$C_6$-cycloalkyl or benzyl, and, in the case where n=2 to 4, is a straight-chain or branched, substituted or unsubstituted alkylene radical or thioalkylene radical having a total of 1 to 8 C atoms, for stabilising organic elastomers against decomposition by oxygen and heat.

$R^1$ and $R^2$ can be, for example: methyl, isopropyl, sec.-butyl, tert.-butyl, cyclopentyl or cyclohexyl.

In the case where n=1, $R^3$ can be, for example, the following radicals: —$CH_3$, —$C_2H_5$, isobutyl, n-hexyl, n-octyl, 2-ethylhexyl, n-decyl, n-dodecyl, n-octadecyl, 3-thia-heptyl or 3-thia-5-methylhexyl.

In the case where n=2 to 4, $R^3$ can be, for example, the following groups: —$CH_2$—, ethylene, tetramethylene, hexamethylene, 3-thia-pentylene,

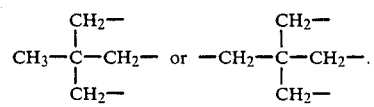

A preferred embodiment of the invention is the use, as stabilisers for elastomers, of those compounds of the formula I in which n=1 and $R^3$ is a hydrocarbon radical which may contain branched molecular groups and may contain —O— or —S— bridges, such as alkyl having in each case a total of 4 to 12 C atoms.

A further preferred embodiment of the invention is the use, as stabilisers for elastomers, of those compounds of the formula I which contain one or more of the following radicals as defined in each case: $R^1$: tert.-butyl, $R^2$: —$CH_3$ or tert.-butyl, X: methylene and $R^3$: $C_4$–$C_{12}$ alkyl.

A further preferred embodiment of the invention is the use, as stabilisers, of those compounds of the formula I in which n=2 and $R^3$ is $C_2$–$C_6$ alkylene.

The compound of the formula II

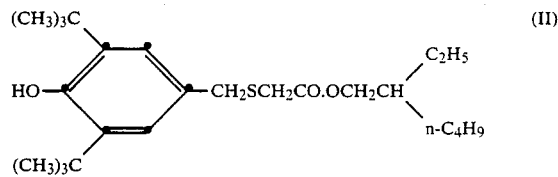

is particularly suitable for use as a stabiliser according to the invention. This use also represents a particular preferred embodiment of the invention.

The stabilisers used according to the invention are added to the organic material to be stabilised in amounts of 0.01 to 10%, preferably 0.05 to 0.5%, based on the total weight of the material to be stabilised.

According to the invention, the following synthetic elastomers are stabilised in particular:

(a) polydienes, preferably polybutadiene, polyisoprene or polychloroprene,
(b) block polymers, preferably the styrene/butadiene/styrene, styrene/isoprene/styrene or styrene/(ethylene-propylene)/styrene types, and
(c) acrylonitrile/butadiene polymers.

If appropriate, these polymers are in the form of latices and can be stabilised as such.

This invention also relates to organic elastomers which contain a compound of the formula I as a stabiliser.

The preparation of the compounds of the formula I is known and has already been described, for example, in German Patent Specification 1,288,604.

The invention also relates to compounds of the formula III

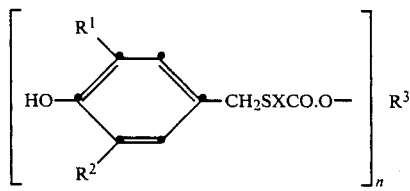

in which n is 1 or 2, $R^1$ is secondary butyl or tert.-butyl and X is methylene or ethylene, and in which $R^3$, in the case where n=1, is a hydrocarbon radical which may contain branched molecular groups and may contain —O— or —S— bridges, such as alkyl having in each case a total of 5 to 12 C atoms, and, in the case where n=2, is a straight-chain or branched alkylene radical having a total of 2 to 4 C atoms. In the case where n=1, $R^3$ can be, for example, n-pentyl, n-hexyl, n-octyl, 2-ethylhexyl, n-decyl, n-dodecyl, 3-thiaheptyl and 3-thia-5-methylhexyl. In the case where n=2, $R^3$ can be, for example, the following groups: ethylene, tetramethylene, hexamethylene and 3-thiapentylene.

Those compounds of the formula III in which n=1 and which contain one or more of the following radicals as defined in each case: $R^1$: tert.-butyl, X: methylene and $R^3$: $C_5$–$C_{12}$-alkyl, constitute a preferred embodiment.

Compounds of the formula III in which n=2 and $R^1$ is tert.-butyl, X is methylene and $R^3$ is $C_2$–$C_6$-alkylene are also preferred.

Quite concrete and particularly preferred compounds of the formula III have the following structures:

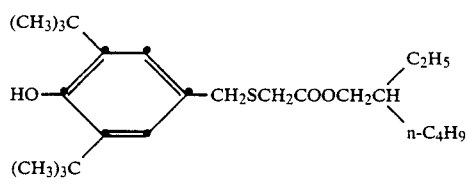

and

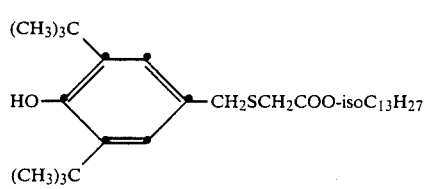

The following substances are further examples of the compounds of the formula III according to the invention:

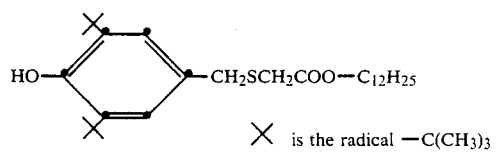

X is the radical —$C(CH_3)_3$

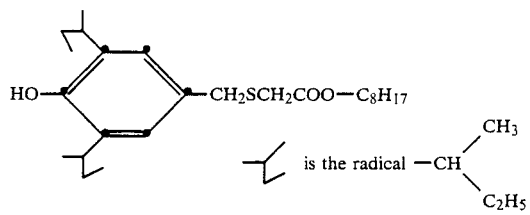

is the radical —CH$\begin{smallmatrix}CH_3\\C_2H_5\end{smallmatrix}$

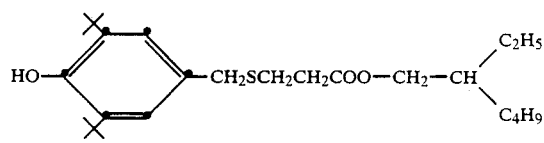

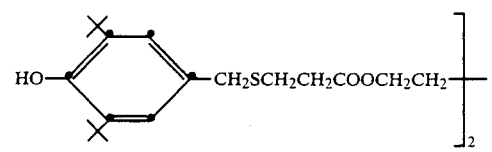

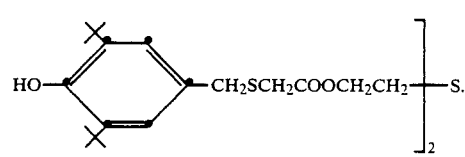

The compounds of the formula III according to the invention are particularly suitable for stabilising organic polymers and lubricants against degradation by oxygen and heat.

The invention thus also relates to the use of these compounds for stabilsing organic polymers and lubricants, and also to organic polymers and lubricants containing in each case a compound of the formula III as a stabiliser against decomposition by oxygen and heat.

More particularly the invention relates to stabilised compositions characterized by incorporating into synthetic elastomers selected from the group consisting of polybutadiene, polyisoprene, polychloroprene, styrene/butadiene/styrene block polymers, styrene/isoprene/styrene block polymers, styrene/(ethylene-propylene)/styrene block polymers and acrylonitrile/-butadiene polymers 0.01 to 10%, based on the total weight of the material to be stabilised, of a phenol-mercapto-carboxylic acid ester of the formula IV

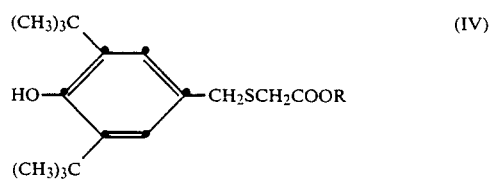

wherein R is $C_1$–$C_{18}$ alkyl.

R can be, for example, methyl, ethyl, isopropyl, n-butyl, isobutyl, tert.-butyl, n-hexyl, n-octyl, 2-ethylhexyl, n-decyl, n-dodecyl, isotridecyl, n-octadeyl. R is preferably branched $C_4-C_{18}$ Alkyl, expecially 2-ethylhexyl (e.g. in formula II) or isotridecyl (e.g. in formula IIa). The isotridecyl residue is derived from tridecylalcohol obtained by oxosynthesis with tetrapropylene.

The compounds of the formula I used according to the invention are suitable for stabilising the following polymers:

1. Polymers of monoolefins and diolefins, for example polyethylene (which may be crosslinked), polypropylene, polyisobutylene, polybut-1-ene, polymethylpent-1-ene, polyisoprene or polybutadiene, and polymers of cycloolefins, for example of cyclopentene or norbornene.

2. Mixtures of the polymers mentioned under (1), for example mixtures of polypropylene with polyethylene or with polyisobutylene.

3. Copolymers of monoolefins and diolefins with one another or with other vinyl monomers, for example ethylene/propylene copolymers, propylene/but-1-ene copolymers, propylene/butadiene copolymers, isobutylene/isoprene copolymers, ethylene/alkyl acrylate copolymers, ethylene/alkyl methacrylate copolymers, ethylene/vinyl acetate copolymers or ethylene/acrylic acid copolymers and their salts (ionomers), and terpolymers of ethylene with propylene and with a diene such as hexadiene, dicyclopentadiene or ethylideneorbornene.

4. Polystyrene.

5. Copolymers of styrene or α-methylstyrene with dienes or acrylic derivatives, for example styrene/butadiene, styrene/acrylonitrile, styrene/alkyl methacrylate or styrene/acrylonitrile/methacrylate; high impact strength mixtures of styrene copolymers and of another polymer, for example a polyacrylate, a diene polymer or an ethylene/propylene/diene terpolymer; and block copolymers of styrene, for example styrene/butadiene/styrene, styrene/isoprene/styrene, styrene-/ethylene-butylene/styrene or styrene/ethylene-propylene/styrene.

6. Graft copolymers of styrene, for example styrene grafted onto polybutadiene, styrene and acrylonitrile grafted onto polybutadiene, styrene and maleic anhydride grafted onto polybutadiene, styrene and alkyl acrylates or alkyl methacrylates grafted onto polybutadiene, styrene and acrylonitrile grafted onto ethylene/propylene/diene terpolymers, styrene and acrylonitrile grafted onto polyalkyl acrylates or polyalkyl methacrylates, or styrene and acrylonitrile grafted onto acrylate/butadiene copolymers, and their mixtures with the copolymers mentioned under (5), for example those known as so-called ABS, MBS, ASA or AES polymers.

7. Halogen-containing polymers, for example polychloroprene, chlorinated rubber or chlorinated or chlorosulfonated polyethylene, in particular polymers of halogen-containing vinyl compounds, for example polyvinyl chloride, polyvinylidene chloride, polyvinyl fluoride or polyvinylidene fluoride, and their copolymers such as vinyl chloride/vinylidene chloride, vinyl chloride/vinyl acetate or vinylidene chloride/vinyl acetate.

8. Polymers derived from α,β-unsaturated acids and from their derivatives, such as polyacrylates and polymethacrylates, polyacrylamides and polyacrylonitriles.

9. Copolymers of the monomers mentioned under (8) with one another or with other unsaturated monomers, for example acrylonitrile/butadiene copolymers, acrylonitrile/alkyl acrylate copolymers, acrylonitrile/vinyl chloride copolymers or acrylonitrile/alkyl methacrylate/butadiene terpolymers.

10. Polymers derived from unsaturated alcohols and amines or from their acyl derivatives or acetals, such as polyvinyl alcohol, polyvinyl acetate, stearate, benzoate or maleate, polyvinylbutyral, polyallyl phthalate or polyallylmelamine.

11. Homopolymers and copolymers of cyclic ethers, such as polyalkylene glycols, polyethylene oxide, polypropylene oxide or their copolymers with bis-glycidyl ethers.

12. Polyacetals such as polyoxymethylene, and polyoxymethylenes which contain comonomers, for example ethylene oxide.

13. Polyphenylene oxides and sulfides.

14. Polyurethanes derived from polyethers, polyesters and polybutadienes with terminal hydroxyl groups on the one hand and aliphatic or aromatic polyisocyanates on the other hand, and their precursors.

15. Polyamides and copolyamides derived from diamines and dicarboxylic acids and/or from aminocarboxylic acids or the corresponding lactams, such as polyamide-4, polyamide-6, polyamide-6,6, polyamide-6,10, polyamide-11, polyamide-12, poly-2,4,4-trimethylhexamethylene terephthalamide, poly-m-phenylene isophthalamide and their copolymers with polyethers, for example with polyethylene glycol, polypropylene glycol or polytetramethylene glycol.

16. Polyureas, polyimides and polyamide-imides.

17. Polyesters derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate or polyhydroxybenzoates, and block polyether/esters derived from polyethers with hydroxyl end groups.

18. Polycarbonates.

19. Polysulfones and polyether-sulfones.

20. Crosslinked polymers derived from aldehydes on the one hand and phenols, urea or melamine on the other hand, such as phenol/formaldehyde, urea/formaldehyde and melamine/formaldehyde resins.

21. Drying and non-drying alkyd resins.

22. Unsaturated polyester resins derived from copolyesters of saturated and unsaturated dicarboxylic acids with polyhydric alcohols, and vinyl compounds as crosslinking agents, and also their halogen-containing, slow-burning, modifications.

23. Crosslinkable acrylic resins derived from substituted acrylic acid esters, for example from epoxyacrylates, urethane-acrylates or polyester-acrylates.

24. Alkyd resins, polyester resins and acrylate resins crosslinked with melamine resins, urea resins, polyisocyanates or epoxide resins.

25. Crosslinked epoxide resins derived from polyepoxides, for example from bis-glycidyl ethers or from cycloaliphatic diepoxides.

26. Natural polymers such as cellulose, natural rubber and gelatine, and their derivatives chemically modified to give homologous polymers, such as cellulose acetates, propionates and butyrates, or the cellulose ethers such as methylcellulose.

The concentration of the stabilisers used according to the invention in the polymers is 0.01 to 10%, preferably 0.05 to 0.5%, based on the total weight of the material to be stabilised.

The stabilisers employed according to the invention can also be used together with other known additives.

Examples of further additives with which it is possible to employ the stabilisers which can be used according to the invention are: 2,6-di-tert.-butyl-4-methylphenol, 4,4'-thio-bis-(6-tert.-butyl-3-methylphenol), 2,2'-methylene-bis-(6-tert.-butyl-4-methylphenol), 2,2'-methylene-bis-(4-methyl-6-cyclohexylphenol), 1,1-bis-(5-tert.-butyl-4-hydroxy-2-methylphenyl)-butane, 1,3,5-tri-(3,5-di-tert.-butyl-4-hydroxybenzyl)-2,4,6-trimethylbenzene, di-(3,5-di-tert.-butyl-4-hydroxybenzyl) sulfide, stearyl 3-(3,5-di-tert.-butyl-4-hydroxyphenyl)-propionate, 1,6-hexanediol bis-3-(3,5-di-tert.-butyl-4-hydroxyphenyl)-propionate, tris-(nonylphenyl) phosphite, distearoyl-pentaerythritol diphosphite, tris-(2,4-di-tert.-butylphenyl) phosphite, di-(2,4-di-tert.-butylphenyl)-pentaerythritol diphosphite and tetrakis-(2,4-di-tert.-butylphenyl) 4,4'-biphenylylenediphosphonite.

The compounds of the formula III are active, even in very small amounts, as antioxidants, corrosion inhibitors and high-pressure additives in lubricants. Thus, mineral and synthetic lubricating oils, and their mixtures, which contain 0.001 to 5% by weight, based on the lubricant, and preferably 0.02 to 3% by weight, of a compound of the formula I have excellent high-pressure lubricating properties which become apparent from greatly reduced wear phenomena on the friction components to be lubricated. The lubricants in question are familiar to those skilled in the art. Examples of such lubricants are to be found, for example, in "Schmiermittel Taschenbuch" ("Lubricants Pocketbook") (Huthig Verlag, Heidelberg, 1974).

The lubricating oil preparation can additionally contain other additives which are added in order to improve certain basic oil properties, such as antioxidants, metal deactivators, rust inhibitors, agents for improving the viscosity index, pour-point depressants, dispersent-detergents and other additives for protection against wear.

Examples of antioxidants are:

(a) Alkylated and non-alkylated aromatic amines and mixtures thereof, for example: dioctyldiphenylamine, mono-tert.-octylphenyl-α-naphthylamine and mono-tert.-octylphenyl-β-naphthylamine, phenothiazine, dioctylphenothiazine, phenyl-α-naphthylamine and N,N'-di-sec.-butyl-p-phenylenediamine.

(b) Sterically hindered phenols, for example 2,6-di-tert.-butyl-p-cresol, 4,4'-bis-(2,6-diisopropylphenol), 2,4,6-triisopropylphenol, 2,2'-thio-bis-(4-methyl-6-tert.-butylphenol) and 4,4'-methylene-bis-(2,6-di-tert.-butylphenol).

(c) Alkyl, aryl or alkaryl phosphites, for example: trinonyl phosphite, triphenyl phosphite and diphenyl decyl phosphite.

(d) Esters of thiodipropionic acid or thiodiacetic acid, for example: dilauryl thiodipropionate or dioctyl thiodiacetate.

(e) Salts of carbamic and dithiophosphoric acids, for example: antimony diamyldithiocarbamate and zinc diamyldithiophosphate.

(f) Combinations of two or more of the above antioxidants, for example: an alkylated amine and a sterically hindered phenol.

Examples of metal deactivators are:

(a) For copper, for example benzotriazole, tetrahydrobenzotriazole, 2-mercaptobenzothiazole, 2,5-dimercaptothiadiazole, salicylidenepropylenediamine and salts of salicylaminoguanidine.

(b) For lead, for example sebacic acid derivatives, quinizarin and propyl gallate.

(c) Combinations of two or more of the above additives.

Examples of rust inhibitors are:

(a) Organic acids and their esters, metal salts and anhydrides, for example: N-oleoyl-sarcosine, sorbitan monooleate, lead naphthenate and dodecenyl-succinic anhydride.

(b) Nitrogen-containing compounds, for example:
  I. Primary, secondary or tertiary aliphatic or cycloaliphatic amines, and amine salts of organic and inorganic acids, for example oil-soluble alkylammonium carboxylates.
  II. Heterocyclic compounds, for example: substituted imidazolines and oxazolines.

(c) Phosphorus-containing compounds, for example: amine salts of phosphoric acid partial esters.

(d) Sulfur-containing compounds, for example: barium dinonylnaphthalene-sulfonate and calcium petroleum-sulfonate.

(e) Combinations of two or more of the above additives.

Examples of agents for improving the viscosity index are: polymethacrylates, vinylpyrrolidone/methacrylate copolymers, polybutenes, olefin copolymers and styryl/acrylate copolymers.

Examples of pour-point depressants are: polymethacrylates and alkylated naphthalene derivatives.

Examples of dispersants/detergents are: polybutenyl-succinic acid imides, polygutenylphosphonic acid derivatives, and superbasic magnesium, calcium and barium sulfonates and phenolates.

Examples of other additives for protection against wear are: compounds containing sulfur and/or phosphorus and/or halogen, such as sulfurised vegetable oils, zinc dialkyldithiophosphates, tritolyl phosphate, chlorinated paraffins and alkyl and aryl disulfides.

The following examples illustrate the invention.

EXAMPLE 1

Stabilisation of acrylonitrile/butadiene/styrene (ABS)

0.7 g of 2-ethyl-n-hexyl 3,5-di-tert.-butyl-4-hydroxybenzyl-mercapto-acetate is dissolved in 40 ml of hexane. The solution is added to a dispersion of 100 g of ABS in 600 g of water, with vigorous stirring. The antioxidant solution is completely absorbed by the ABS in a short time (1 minute). The ABS powder is filtered off with suction and dried in vacuo for 40 hours at 40° C. 2% of titanium dioxide (pigment) and 1% of ethylene-bis-stearic acid amide (lubricant) are added to the dry powder. The mixture is then compounded for 4 minutes on a two-roll mill at 180° C. The rolling hide is pressured at 175° C. to form a 0.8 mm thick plate, from which test pieces of dimensions 45×17 mm are stamped.

The plate without the compound according to the invention is produced in the same way.

The effectiveness of the additive added is tested by heating ageing in a circulating air oven at 200° C. The colour development after a testing period of 30 minutes is used as the criterion. The colour intensity is quantified with the "Yellowness Index" according to ASTM D 1925. Higher numbers denote a more intense yellow impression. The experiments show that the colour development is effectively suppressed by the additive added.

| | Yellowness Index after 30 minutes |
|---|---|
| Without stabiliser | 47 |
| 0.7% of 2-ethyl-n-hexyl 3,5-di-tert.-butyl-4-hydroxybenzyl-mercapto-acetate | 36 |

EXAMPLE 2

Stabilisation of polybutadiene rubber 100 parts of polybutadiene which has been stabilised beforehand with 0.36% of 2,6-di-tert.-butyl-p-cresol are kneaded for 30 minutes in a Brabender plastograph, at 150° C. and 60 rpm, together with 0.05, 0.1 and 0.2% of 2-ethyl-n-hexyl 3,5-di-tert.-butyl-4-hydroxybenzyl-mercapto-acetate.

The gel content of the material found after processing in the Brabender plastograph is used as the criterion for the effectiveness of the additive added. This gel content is determined as follows.

1 gram of polybutadiene is dissolved in 100 ml of toluene overnight, at room temperature. The solution is filtered through glass wool and the filtered solution is evaporated to dryness. The gel content is given by:

$$\text{gel} = \frac{E - A}{E} \times 100 \, (\%)$$

E = weighed portion (1 gram)
A = weight of the evaporation residue.

The experiment shows the effective suppression, by the additive added, of gel development during processing.

| | Gel content % |
|---|---|
| Without stabiliser | 50 |
| 2-Ethyl-n-hexyl 3,5-di-tert.-butyl-4-hydroxybenzyl-mercapto-acetate | |
| 0.05% | 22 |
| 0.1% | 12 |
| 0.2% | 5 |

EXAMPLE 3

Stabilisation of polybutadiene rubber 100 parts of polybutadiene which has been stabilised beforehand with 0.36% of 2,6-di-tert.-butyl-p-cresol are plasticised for 6 minutes in a two-roll mill, at 50° C., together with 0.1 or 0.2%, respectively, of 2-ethyl-n-hexyl 3,5-di-tert.-butyl-4-hydroxybenzyl-mercapto-acetate.

The rolling hides are pressed at 60° C. to form 10 mm thick plates. The plate without the compound according to the invention is produced in the same way.

The effectiveness of the additive added is tested by heat ageing in a circulating air oven at 80° C. The gel content found during ageing in the oven is used as the criterion. (Determination as in Example 2.) After an induction period, the gel content rapidly increases. The time after which a gel content of 5% has been reached is used as an arbitrary definition of the induction period.

The experiment shows that the induction times can effectively be prolonged by the additive added.

| | Induction time in weeks until 5% of gel has been reached |
|---|---|
| Without additive | 3 |
| 2-Ethyl-n-hexyl 3,5-di-tert.-butyl-4-hydroxybenzyl-mercapto-acetate | |
| 0.1% | 7 |
| 0.2% | 11 |

EXAMPLE 4

Stabilisation of polybutadiene rubber

The procedure of Example 3 is repeated, except that the material used contains no stabiliser from manufacture.

The time after which a gel content of 1% has been reached is defined as the induction period.

| | Induction time in days until 1% of gel has been reached |
|---|---|
| Without stabiliser | 10 |
| 2-Ethyl-n-hexyl 3,5-di-tert.-butyl-4-hydroxybenzyl-mercapto-acetate | |
| 0.2% | 48 |

EXAMPLE 5

Stabilisation of polybutadiene rubber

The test pieces of Example 4 are additionally aged by immersion in silicone oil at 160° C. for 20 minutes. The gel content at the end of the ageing is used as the criterion.

The experiments show the effective suppression, by the additive added, of gel development during ageing.

| | Gel content % |
|---|---|
| Without additive | 88 |
| 0.2% of 2-ethyl-n-hexyl 3,5-di-tert.-butyl-4-hydroxybenzyl-mercapto-acetate | 6 |

The subject of the invention "Compounds of the formula III" is illustrated in greater detail in Example 6.

EXAMPLES 6 to 14

Substrate: prestabilised BR Solprene 250 ® (Phillips Petroleum).

Incorporation and sample production:

The additives are incorporated at 50° C. in a roll mill. 2 mm and 10 mm plates are then pressed at 80° C. in a hydraulic heating press. Ageing procedures:

(a) Ageing in an oven at 80° C. with 10 mm plates in a HORO circulating air oven; periodic determination of the gel at room temperature in toluene.

(b) Ageing in a Brabender plasticorder at 160° C. and 60 rpm for 30 minutes. Determination of the induction time ($T_{ind}$) in minutes (time until the torsional moment rises 100 meterpond above the minimum); gel determination in toluene after ageing; colour measurement of 2 mm samples of the aged material.

(c) Ageing of 2 mm samples at 160° C. for 30 minutes in silicone oil; determination of the gel content at room temperature in toluene.

(d) Determination of the coloration by measurement of the Yellowness Index according to ASTM D 1925-70, during 10-week storage of 2 mm samples (A) in diffuse daylight, (B) in the dark and (C) at 80° C. in a circulating air oven.

Results of the ageing experiments

| Example No. | Stabilizer | Concentration % | Oven, 80° C. Weeks until gel->5% | Brabender, 160° C. 60 rpm, 30 minutes $T_{ind}$ (minutes) | Gel % | YI | Gel in % after ageing in silicone oil at 160° C. 30 minutes | Maximum Yellowness Index for 10-weeks storage Daylight | Darkness | Oven, 80° C. |
|---|---|---|---|---|---|---|---|---|---|---|
| 6 | HO—⟨×,×⟩—$CH_2SCH_2CO_2$-iso-$C_8H_{17}$ | 0.1 | 8 | 11.3 | 43 | 31 | 4.8 | 9 | 9 | 110 |
|   |   | 0.25 | 13 | 14.8 | 29 | 25 | 4.4 | 9 | 8 | 34 |
|   |   | 0.5 | 16 | 17.5 | 19 | 16 | 2.8 | 9 | 9 | 17 |
| 7 | HO—⟨×⟩(CH_3)—$CH_2SCH_2CO_2$-iso-$C_8H_{17}$ (1) | 0.1 | 8 | 9.3 | 50 | 28 | 4.9 | 10 | 10 | 98 |
|   |   | 0.25 | 10 | 8.5 | 43 | 34 | 4.3 | 11 | 9 | 36 |
|   |   | 0.5 | 12 | 8.0 | 47 | 32 | 2.2 | 9 | 10 | 27 |
| 8 | HO—⟨CH_3,CH_3⟩—$CH_2SCH_2CO_2$-iso-$C_8H_{17}$ | 0.1 | 7 | 9.3 | 51 | 33 | 7.4 | 10 | 9 | 108 |
|   |   | 0.25 | 7 | 6.5 | 48 | 38 | 5.1 | 10 | 9 | 35 |
|   |   | 0.5 | 7 | 5.8 | 51 | 38 | 3.4 | 9 | 9 | 27 |
| 9 | HO—⟨×,×⟩—$CH_2SCH_2CO_2C_{18}H_{37}$ | 0.1 | 8 | 10.8 | 47 | 29 | 9.4 | 10 | 11 | 128 |
|   |   | 0.25 | 12 | 12.5 | 37 | 27 | 5.6 | 11 | 10 | 83 |
|   |   | 0.5 | 16 | 14.0 | 21 | 25 | 3.1 | 10 | 8 | 20 |
| 10 | HO—⟨×,CH_3⟩—$CH_2SCH_2CO_2C_{18}H_{37}$ | 0.1 | 8 | 8.3 | 51 | 30 | 11.4 | 8 | 11 | 101 |
|   |   | 0.25 | 9 | 9.5 | 47 | 32 | 4.3 | 9 | 11 | 75 |
|   |   | 0.5 | 8 | 9.0 | 45 | 31 | 1.2 | 11 | 10 | 34 |
| 11 | HO—⟨CH_3,CH_3⟩—$CH_2SCH_2CO_2C_{18}H_{37}$ | 0.1 | 6 | 7.8 | 55 | 37 | 11.5 | 13 | 15 | 100 |
|   |   | 0.25 | 6 | 6.8 | 59 | 37 | 9.2 | 13 | 14 | 76 |
|   |   | 0.5 | 7 | 7.3 | 56 | 37 | 9.6 | 14 | 14 | 33 |
| 12 | (HO—⟨×,×⟩—$CH_2SCH_2CO_2CH_2CH_2CH_2)_2$ | 0.1 | 6 | 11.5 | 53 | 29 | 2.0 | 11 | 9 | 115 |
|   |   | 0.25 | 8 | 11.5 | 52 | 32 | 1.2 | 12 | 10 | 59 |
|   |   | 0.5 | 12 | 11.0 | 52 | 35 | 0.7 | 12 | 9 | 25 |
| 13 | (HO—⟨×,CH_3⟩—$CH_2SCH_2CO_2CH_2CH_2CH_2)_2$ | 0.1 | 8 | 9.5 | 47 | 30 | 2.2 | 10 | 10 | 96 |
|   |   | 0.25 | 9 | 9.5 | 51 | 32 | 0.3 | 10 | 11 | 30 |
|   |   | 0.5 | 10 | 9.5 | 50 | 31 |   | 12 | 12 | 23 |
| 14 | (HO—⟨×,×⟩—$CH_2SCH_2CO_2$-iso-$C_{13}H_{27}$ | 0.5 | 13 | 15.5 | 11 | 25 | 3.3 | —(2) | —(2) | 25 |
|   | without (control) | — | 6 | 8.8 | 58 | 33 | 12.3 | 10 | 8 | 102 |

(1) ✕ denotes: —$C(CH_3)_3$
ISO-$C_8H_{17}$ denotes 2-ethylhexyl
(2) not tested

EXAMPLE 14

Action of 2-ethyl-n-hexyl 3,5-di-tert.-butyl-4-hydroxy-benzyl-mercapto-acetate in prestabilised polyisoprene Substrate: Cariflex IR 305 ® (contains about 0.13% of BHT) (Shell)

Incorporation: Roll mill at 60° C.

Sample production: 10 mm thick plates pressed at 90° C. for 15 minutes:

Ageing: Circulating air oven at 70° C.

Ageing criterion: Change in the Mooney viscosity (decrease).

|  | Mooney viscosity ML 1' + 4' (100° C.) after days | | | | | |
|---|---|---|---|---|---|---|
|  | 0 | 7 | 14 | 21 | 28 | 35 |
| Without stabiliser | 69 | 49 | 36 | 25 | | |
| 0.2% of stabiliser | 69 | 60 | 50 | 50 | 41 | 39 |

EXAMPLE 15

Action of 2-ethyl-n-hexyl 3,5-di-tert.-butyl-4-hydroxybenzyl-mercapto-acetate in unstabilised SBR polymerised in emulsion Substrate: Polysar ® SBR latex polymerised in emulsion (Shell)

Incorporation: Dissolution of the stabilisers in a small amount of acetone and careful incorporation into the latex by stirring.

Coagulation: Dropwise addition of the latex to 0.35% aqueous $CaCl_2$ solution at 90° C., with vigorous stirring; washing twice with distilled water; drying in vacuo at 40° C. Sample production: 10 mm thick plates pressed at 80° C. for 15 minutes.

Ageing: Oven at 80° C.

Ageing criterion: Increase in the Mooney viscosity.

|  | Mooney viscosity ML 1' + 4' (100° C.) after weeks | | | | | | |
|---|---|---|---|---|---|---|---|
|  | 0 | 1 | 2 | 3 | 4 | 5 | 6 |
| Without stabiliser | 55 | 60 | 68 | 94 | | | |
| 0.3% of the stabiliser indicated above | 54 | 53 | 52 | | 55 | 55 | 74 |
| 0.3% of Wingstay L ®[1] | 54 | 55 | 61 | 72 | 85 | | |
| 1.25% of Wingstay S ®[2] | 56 | 80 | 92 | 107 | | | |
| 0.75% of Naugawhite liq ®[3] | 56 | 53 | 58 | 65 | 78 | 85 | |

EXAMPLE 16

Action of 2-ethyl-n-hexyl 3,5-di-tert.-butyl-4-hydroxybenzyl-mercapto-acetate in an SBS shoe sole compound Formulation: SBS Europrene T 171 ® (100 parts of SBS + 50 parts of oil) from

| Anic | 150 parts by weight |
|---|---|
| Kristallpolystyrol N 168 ® (BASF) | 30 parts by weight |
| Oel Talpa 945 ® (Shell) | 20 parts by weight |
| Ultrasil VN 3 ® (Bayer) | 10 parts by weight |

Preparation of the mixture and incorporation of the stabilisers: in a mill at 160° C.

Sample production: Pressing of 0.5 mm plates at 130° C., 10 minutes; stamping out of ISO S 2 dumb-bell test bars.

Ageing: Cell-type oven at 70° C.

Test: Determination of tensile strength (kp/cm²) and elongation (%) by a tensile test.

| Stabiliser | Tensile strength in kp/cm² after weeks | | | | | Elongation in % after weeks | | | | |
|---|---|---|---|---|---|---|---|---|---|---|
|  | 0 | 4 | 6 | 10 | 14 | 0 | 4 | 6 | 10 | 14 |
| without | 101 | 30 | | | | 640 | 300 | | | |
| 0.2% of the above stabiliser | 110 | 101 | 99 | 96 | 83 | 650 | 600 | 585 | 570 | 550 |
| 0.2% of methyl 3,4-di-tert.-butyl-4-hydroxybenzyl-mercapto-acetate | 104 | 100 | 99 | 88 | 80 | 620 | 600 | 590 | 530 | 520 |
| 0.4% of Topanol OC ® 0.8% of trinonylphenyl phosphite | 95 | 78 | 64 | 40 | | 620 | 252 | 465 | 330 | |

The subject of the invention "Compounds of the formula III" is illustrated in greater detail in Example 17.

EXAMPLE 17

2-Ethyl-n-hexyl 3,5-di-tert.-butyl-4-hydroxybenzyl-mercapto-acetate.

26.3 g of 2,6-di-tert.-butylbenzyl-dimethylamine, 20.4 g of the ethyl-n-hexyl ester of thioglycol and 50 ml of dimethylformamide are heated for 2 hours at 120° C. under nitrogen, with stirring. Dimethylamine escapes. In the thin layer chromatogram (TLC), virtually no further educts can then be detected. The solvent is removed in vacuo and the viscous residue is dissolved in 100 ml of ligroin. After washing with water, the dried ligroin solution is decolorised by treatment with 1 g of "Hyflow Supercel" kieselguhr (Jons Manville Sales Corp.) and filtered until the filtrate is clear, and the solvent is removed in vacuo.

This yields 38.5 g of the product of this example, in the form of an almost colourless, viscous oil, which solidifies to form crystals on prolonged standing at about 20° C. and which is defined by elementary analysis and TLC.

Result of the elementary analysis: $C_{25}H_{42}O_3S$ (422.67); C calculated 71.04; found 71.00. H calculated 10.02; found 9.90. S calculated 7.59; found 7.70.

EXAMPLE 18

The oil oxidation test, standard version according to ASTM D 2272 (Rotary Bomb Oxidation Test), is carried out in the following way. An oil sample of 50 ml of Vitrea 100 ® mineral oil from SHELL is oxidised in an oxygen atmosphere, in a glass vessel, together with 5 ml of distilled water and a polished, catalytically active Cu spiral washed with petroleum ether, 0.25 g of the stabiliser according to Example 17 being added.

The glass vessel is in a stainless steel bomb with a manometer. The bomb rotates axially at 100 rpm, at an angle of 30° to the horizontal, in an oil bath at 150° C. The oxygen pressure is initially about 6 bars, before heating, increases to exactly 14 bars at 150° C. and remains constant until oxidation has started. The test has ended when there has been a pressure decrease of 1.7 bars. The time is recorded in minutes.

| Stabiliser | Result<br>Minutes until pressure decrease of 1.7 bars |
| --- | --- |
| without | 16 |
| according to Example 17 | 101 |

EXAMPLE 19

The oil oxidation test is carried out in a modified version according to IP 280, i.e. "CIGRE".

Conditions: Introduction of oxygen for 4 hours at 150° C. (4 liters of $O_2$/hour).

Determination of the acid number after the test has ended; tabulated value: mg of KOH consumed per g of test oil.

Stabiliser concentration: 0.5% by weight
Test oil: "Vitrea 100" mineral oil from SHELL.

| Stabiliser | Result<br>mg of KOH/g |
| --- | --- |
| without | 3.6 |
| according to Example 17 | 0.59 |

What is claimed is:

1. A lubricant composition comprising mineral oil or synthetic oil or mixture thereof and an effective stabilizing amount of a compound of the formula

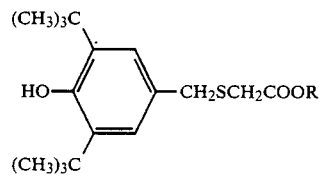

wherein R is $C_8$–$C_{13}$ alkyl.

2. The composition of claim 1, wherein R is 2-ethylhexyl.

3. The composition of claim 1, wherein R is isotridecyl.